United States Patent [19]

Kurtz et al.

[11] 4,128,351
[45] Dec. 5, 1978

[54] STERNOTOMY SURGICAL NEEDLE

[75] Inventors: Leonard D. Kurtz, Woodmere; Philip Ludwig, Merrick, both of N.Y.

[73] Assignee: Deknatel Inc., Queens Village, N.Y.

[21] Appl. No.: 787,984

[22] Filed: Apr. 15, 1977

[51] Int. Cl.² .............................................. A61B 17/32
[52] U.S. Cl. ................................... 128/305; 128/339; 30/168
[58] Field of Search ............... 128/339, 305; 30/164.9, 30/168; 142/42; 145/25

[56] References Cited

U.S. PATENT DOCUMENTS

| | | | |
|---|---|---|---|
| 3,106,019 | 10/1963 | Magnussen | 30/168 |
| 3,197,997 | 8/1965 | Kurtz | 128/339 X |
| 3,636,955 | 1/1972 | Kurtz | 128/339 |

*Primary Examiner*—Stephen C. Pellegrino
*Attorney, Agent, or Firm*—Larson, Taylor and Hinds

[57] ABSTRACT

An improved surgical needle of the type having a simple main cutting edge extending across the needle and formed by the intersection of two planar surfaces for use in cutting through hard body tissue material. The forward end of the needle includes a relatively small third substantially planar surface having an acute angle of convergence with the axis of the needle and intersecting at substantially equal acute angles with the other two planar surfaces. The surgical needle is preferably curved in the reference plane defined by the main cutting edge and the axis of the needle. Such an improved surgical needle results in an extremely sharp needle with a high resistance to burring.

8 Claims, 11 Drawing Figures

U.S. Patent  Dec. 5, 1978  Sheet 2 of 2  4,128,351
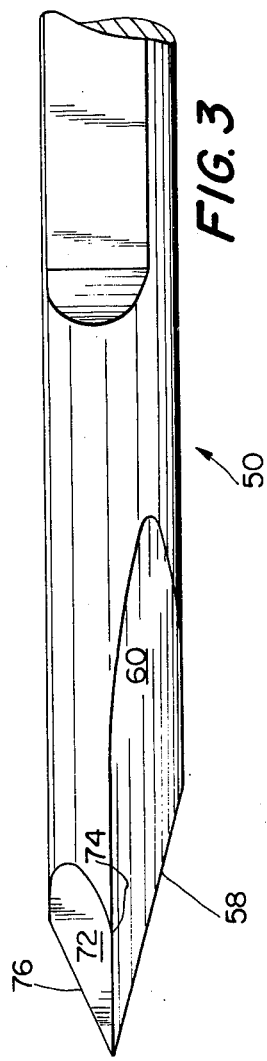
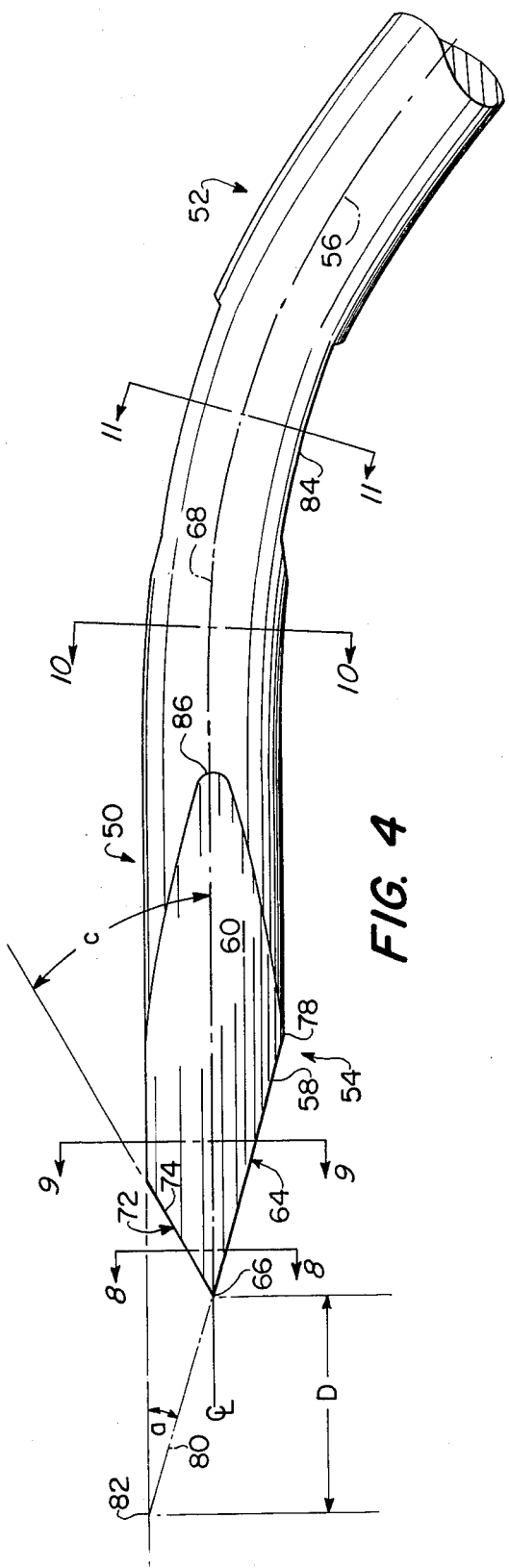
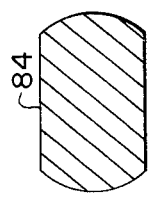
FIG. 11
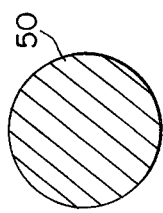
FIG. 10
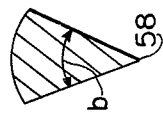
FIG. 9
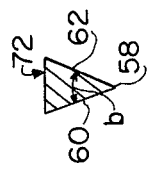
FIG. 8

STERNOTOMY SURGICAL NEEDLE

FIELD OF THE INVENTION

This invention relates to surgical cutting instruments and in particular relates to an improved surgical needle for suturing through calcified tissue, cartilage, or bone.

DESCRIPTION OF THE PRIOR ART

A surgical cutting instrument, as is well known, has the concomitant requirements of being as sharp as possible in order to perform its function properly and of being resistant to burr formation caused by an insufficient amount of metal at the extreme tip portion of the needle. In the previous Kurtz U.S. Pat. Nos. 2,869,550 and 3,094,123, issued Jan. 20, 1959 and June 18, 1963, respectively, a sharp surgical needle was disclosed, which needle has a single main cutting edge formed by the intersection of two planar surfaces such that the main cutting edge extends from one side of the needle to the other side thereof. In this type of needle, greater sharpness is obtained by decreasing the slope angle of the main cutting edge relative to the needle axis. However, as discussed in the Kurtz U.S. Pat. No. 3,636,955 issued Jan. 25, 1972, as the slope angle is decreased, a point is reached at which so little material is left at the point that the point lacks sufficient structural integrity to effectively penetrate the tissue without the tip of the point burring or otherwise deforming.

In the Kurtz U.S. Pat. No. 3,094,123, the concept of blunting the tip of the needle to avoid deformation of the tip, even when using a fairly sharp slope angle, was disclosed. The Kurtz U.S. Pat. No. 3,636,955 discloses the concept of adding a third planar surface at the extreme tip so as to form a chisel-type forward cutting edge at the intersection of the third planar surface with one of the first two planar surfaces. Unfortunately, as the structural strength of the tip portion of the needle has been increased by providing more metal at this area by using either a rounded tip or a chisel-type tip, the amount of force to obtain needle penetration has been increased, particularly when calcified tissue must be penetrated. Thus, there exists a need for a surgical needle having a very sharp point and which is still strong enough to retain its structural integrity when used to cut through bone or other hard tissue.

The principal factors determining the amount of force required in needle penetration of tissue include the force required for the engagement of the tip of a needle and for the widening of the hole. The widening of the hole is effected either by the blunt dilatation of a conventional taper point needle or by a very sharp cutting action, as occurs with a needle of the type disclosed in the Kurtz U.S. Pat. No. 2,869,550 or by the relatively sharp cutting action as with a conventional cutting edge needle, or with a combination of the three. With a taper point needle, after the tip is engaged, a hole is made by pure blunt dilatation with no cutting action whatsoever. After the hole is fully developed, the rest of the shaft slides through and the suture, attached to the needle, follows. On the other hand, with a needle of the type disclosed in the Kurtz U.S. Pat. No. 2,869,550, a hole is produced by initially engaging the tip. The cutting edge of this needle then enlarges the hole. Finally, the remainder of the hole size is made by blunt dilatation with no cutting edge being present. When the hole is fully developed, the rest of the shaft slides through with friction as the major resistance component. Still further, with a conventional cutting edge needle, the relatively sharp edges slide through, after the tip is engaged, until there is a fully developed hole. After the hole is developed, the shaft slides through with the major resistance component being only friction.

The dilatation per unit time is a direct reflection of the work required, and hence the force required, for the needle to make the fully developed hole. With a taper point, the included angle (at the apex of the cone) is approximately 12°. When the needle included angle is more acute, less work per unit time would be required to make a fully developed hole. However, the more acute the angle, the more fragile the tip with resultant possible bending over and burr formation. Burr formation obviously destroys the sharpness of the needle. When the angle is greater than 12°, the dilatation per unit time must be faster and the needle appears to be more blunt because of the necessity for rapid dilatation.

With respect to the needle of the type disclosed in U.S. Pat. No. 2,869,550, it is obvious that the longer the knife blade, the less metal there is at the tip and the greater the danger of turning the tip with burr formation. In the past, when this type needle had to be used for hard tissue material, the tip edge was blunted as disclosed in the Kurtz U.S. Pat. No. 3,094,123 in order to allow a long cutting action. Similar reasoning applies for the conventional cutting edge needles of the type fully discussed in the Kurtz U.S. Pat. No. 2,869,550. The longer the edge which slip through tissue on entering, the sharper the needle and the less required force per unit time to make a completely developed hole. The reasons for desiring an extremely sharp needle with structural integrity is discussed in detail in the afore-cited Kurtz U.S. patents. A sharper needle results in a smaller opening and a minimization of trauma. Obviously, needles which break or bend while in use or which tear through tissue are undesirable. On the other hand, it is very desirable to have needles which require minimum force when penetrating tissue.

SUMMARY OF THE INVENTION

Thus, a purpose of the present invention is to provide a surgical cutting instrument which is both sharp enough and strong enough to cut through hard body tissue without burring or otherwise becoming deformed at its point and which requires a minimum amount of force in its use.

According to the present invention, there is provided a surgical cutting instrument having a main cutting edge extending from one side of the needle to a point near the other side thereof and passing through the axis of the needle, the main edge being formed by the intersection of two planar surfaces. As a matter of convention, the side of the needle having the main cutting edge is referred to as the "bottom" of the needle and the plane defined by the main cutting edge and the axis of the needle point or tip is referred to as the "reference plane," so that when the main edge is on the bottom, the reference plane is vertical. It is apparent, however, that the needle could assume any orientation in practice.

It is an object of the present invention to form a new improved surgical cutting needle for cutting through bone or other hard tissue which overcomes the disadvantages of previously known surgical cutting needles. It is also an object of the present invention to provide a surgical needle that has sufficient metal at the tip to minimize the danger of burr formation, has a long knife blade, has longer edges which slip through the tissue on entering, and requires less force per unit time to make a completely developed hole.

A surgical needle according to the present invention has an extremely long cutting edge formed by the intersection of two substantially planar surfaces and a secondary cutting edge having a different, sharper angle and which is located proximate to the tip of the needle. Such a needle permits as long a cutting action as possible, yet has a greatly decreased possibility for burr formation. Thus the resultant needle has two differently shaped cutting edge points, the main cutting edge being as long as possible and the secondary cutting edge being blunter and confined close to the tip of the needle.

In a presently preferred embodiment of the invention, the surgical instrument comprises a curved body portion and a cutting tip portion. The axis of the curved body portion defines a reference plane. The cutting tip portion has a main cutting edge that is formed by the intersection of first and second substantially planar surfaces, the main cutting edge lying in the reference plane and on a line which intersects the needle axis. A third planar surface intersects the first and second planar surfaces so as to form corresponding acute angles therewith and a forward end point that is located within the fictive circumferential boundaries of the tip portion.

The foregoing and other objects and attendant advantages of the present invention are discussed in or will become apparent from the detailed description of the preferred embodiment hereinbelow.

BRIEF DESCRIPTION OF THE DRAWINGS

In the drawings in which like numerals represent like elements in the several views:

FIG. 3 is a perspective view illustrating the tip portion of a surgical cutting needle and showing the features of the present invention.

FIG. 4 is a side elevational view of the surgical cutting needle according to the present invention.

FIG. 8 is a cross-sectional view taken along line 8—8 of FIG. 4.

FIG. 9 is a cross-sectional view taken along line 9—9 of FIG. 4.

FIG. 10 is a cross-sectional view taken along line 10—10 of FIG. 4.

FIG. 11 is a cross-sectional view taken along line 11—11 of FIG. 4.

DETAILED DESCRIPTION OF THE PREFERRED EMBODIMENT

Figure 1:
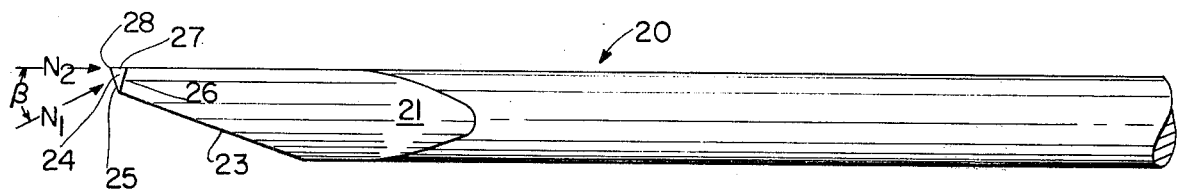
FIG. 1 illustrates the tip portion of a conventional surgical cutting needle in side elevation.
Figure 2:
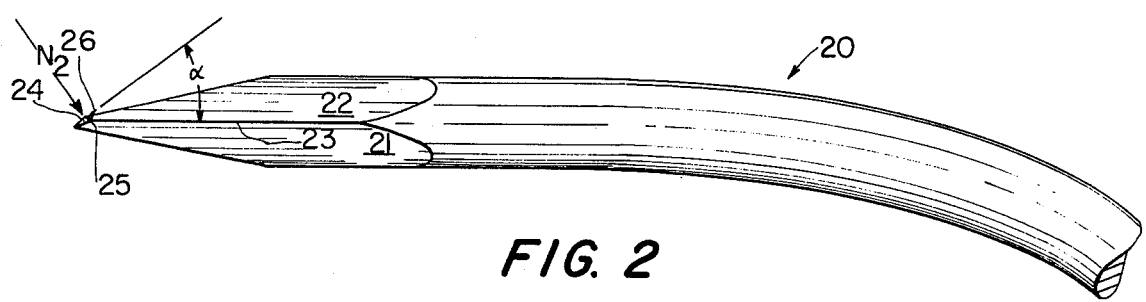
FIG. 2 is a bottom view of the conventional surgical cutting needle, the tip portion of which is depicted in FIG. 1.
Figure 5:
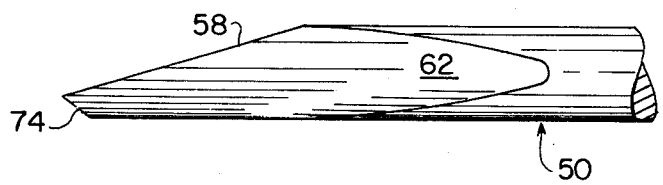
FIG. 5 is an elevational enlarged view of the cutting portion of an actual surgical needle according to the present invention.

With reference to FIGS. 1 and 2, a prior art surgical needle as disclosed in the Kurtz U.S. Pat. No. 3,636,955 is depicted at 20. Needle 20 includes the two conventional planar surfaces 21 and 22 which form the main cutting edge 23 known heretofore. A third planar surface 24 forms an angle other than 90° with the reference plane of the needle. Third surface 24 intersects planar surface 22 at its forward side to form a chisel-type forward cutting edge 25, and it intersects the first planar surface 21 at its second or rearward side to form a rearward edge 26. The intersection of third surface 24 with the outer periphery of needle 20 is shown at 27. The plane of third surface 24 forms a complex angle with the axis of the needle and is inclined rearwardly by an angle $\alpha$. This will assure that the forward cutting edge 25, which as previously indicated is formed by the intersection of the third surface 24 and the second planar surface 22, slopes rearwardly as well as downwardly. Angle $\alpha$ can be approximately 45°. Additionally, to provide a slightly sharper point of introduction, third surface 24 is inclined rearwardly, the downward component being illustrated by the angle $\beta$ in FIG. 1. The two arrows indicated by $N_1$ and $N_2$ represent the components of the lines normal to third surface 24 taken in the vertical and horizontal planes, respectively.

Needle 20 is curved in an arc in the plan view of the needle such that cutting edge 23 extends laterally. In addition, as seen in FIG. 1, the tip of the needle 20, shown at 28, is on the periphery of the needle. In effect then, planar surface 24 merely blunts the end of needle 20 and does not provide a knife-type cutting edge, but rather provides a chisel-type cutting edge.

Figure 6:
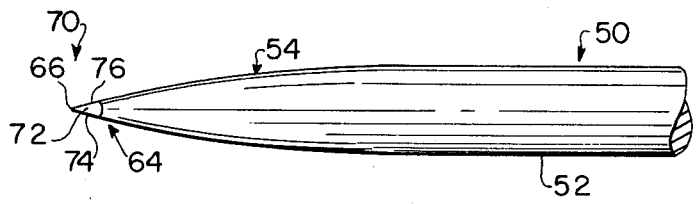
FIG. 6 is a top plan view of FIG. 5.
Figure 7:
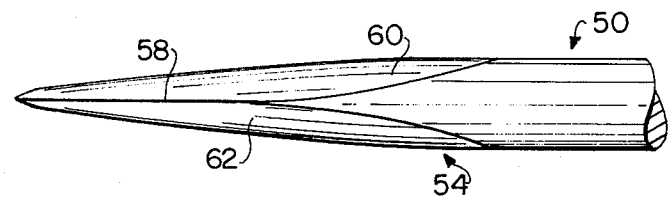
FIG. 7 is a bottom plan view of FIG. 5.

A surgical needle 50 according to the present invention is illustrated in FIGS. 3 through 11. Needle 50 includes a body portion 52 and a cutting portion 54 and has a curved axis 56 which defines a reference plane. A main cutting edge 58 is formed in a conventional manner by the intersection of a first substantially planar surface 60 and a second substantially planar surface 62 (FIG. 7). Thus it can be seen that main cutting edge 58 lies in the reference plane as shown in FIG. 4.

Cutting portion 54 includes an end portion 64 having a tip 66 and a longitudinal axis 68 which is a continuation of needle axis 56. End portion 64 is comprised of a blunt cutting edge portion 70 (FIG. 6) which is formed by the intersection of a third substantially planar surface 72 (FIG. 3) with first and second surfaces 60 and 62, thereby forming secondary cutting edges 74 and 76 (FIG. 6). As seen in FIG. 4, main cutting edge 58 extends from the outer periphery at point 78 of needle 50 forwardly toward tip 66 at the intersection of third surface 72. Thus, main cutting edge 58 is truncated by third surface 72 and if extended, as shown by dashed line 80 would intersect with the outer periphery of needle 50 at fictive intersection 82. The longitudinal distance between fictive intersection 82 and tip 66 represents the missing portions of needle 50.

First, second and third surfaces 60, 62, and 72 are preferably formed by grinding. In this way, the diameter of the point does not become larger than the diameter of the rest of the needle. Other advantages resulting from grinding the needle are discussed in the three aforementioned Kurtz U.S. patents.

FIGS. 8 through 11 depict the cross-sectional shapes of needle 50 at various locations along body portion 52 and cutting portion 54. Needle 50 is generally round (FIG. 10) with a flat section at 84 (FIG. 4) to provide a needle holder (see e.g. Kurtz U.S. Pat. No. 3,265,070). Cutting portion 54 begins at the rearward terminus 86 of surfaces 60 and 62. The rearward terminus of end portion 64 has a generally wedge-shape cross-section (FIG. 9) with an arcuate top while the forward part of end portion 64 has a triangular wedge shape cross-section (FIG. 8).

With reference to FIG. 4, the angle between main cutting edge 58 and the upper, outer periphery of needle 50 is identified as angle "a" and is termed the angle of slope. This angle determines the rate at which the tissues are cut to the diameter of the needle. The angle shown as angle "b" in FIG. 8 is termed the sharpness angle. This angle actually determines the sharpness of main cutting edge 58. It is apparent that if the sharpness angle is made too small, there is insufficient metal in the point to give the point the necessary strength. Similarly, the angle of slope must be minimized to provide for ease of passage of the needle through the tissue and yet must be sufficiently large to preserve metal at the point of tip 66 to give the needle rigidity. (See Kurtz U.S. Pat. No. 2,869,550 for ranges of the sharpness angle, and angle of slope). In the present invention, it is preferable that the angle of slope "a" be less than 20° and preferably 18°. The present needle 50 performs the best when the sharpness angle is within the range of 40° to 50°, inclusive, and preferably is approximately 43°.

Third surface forms an acute angle of convergence "c" with axis 68 resulting in tip 66 being within the fictive periphery of end portion 64, the periphery being outlined by dashed lines FIG. 4. Angle of convergence "c" can be from 20° to 35° and is preferably 30°. As third surface 72 is ground, the length of needle 50 is actually shortened as the needle is advanced into the grinding wheel. The amount of advancement of needle 50 is shown by the distance D in FIG. 4 and can be from 0.020 inch to 0.125 inch. As is clearly seen, the greater the amount of advancement D at the same angle of convergence c, the lower will be the resulting location of tip 66. It must be appreciated that third surface 72 is relatively small with respect to first and second surfaces 60 and 62. The resulting secondary cutting edges 74 and 76 are usually no more than one-fifth to one-sixth the length of main cutting edge 58. Nevertheless, the addition of third surface 72 to a conventional single cutting edge needle adds a significant amount of metal at the tip portion and amazingly provides a greatly reinforced tip with a major resistance to burring when needle 50 is used in hard tissue. Thus, the provision of a blunter cutting edge portion confined as close to tip 66 as possible and forming an acute angle with main cutting edge 58, together with main cutting edge 58 being as long as possible, results in a greatly improved needle having a high resistance to burring, and a low insertion and penetration force requirement, and thus creating a minimal amount of trauma to the tissue.

Although the invention has been described in considerable detail with respect to a preferred embodiment thereof, it should be apparent that the invention is capable of numerous modifications and variations by those skilled in the art without departing from the spirit and scope of the invention.

We claim:

1. A surgical instrument comprising a body portion and a cutting portion, a pair of intersecting first and second planar surfaces forming a single main cutting edge extending from one side of the cutting portion of the instrument to a point at the end of the instrument, a third planar surface having an acute angle of convergence with the longitudinal axis of the instrument and extending from the opposite side of the cutting portion of the instrument to the point thereof, secondary cutting edges formed by the intersection of the third planar surface with said pair of first and second planar surfaces, the point at the end of the instrument being on the single main cutting edge so that the end portions of both the main and secondary cutting edges extend to the end point of the instrument.

2. A surgical insstrument as claimed in claim 1 wherein said surgical instrument is curved in the reference plane defined by said main cutting edge and said axis.

3. A surgical instrument as claimed in claim 1 wherein said main cutting edge forms an acute angle with said third surface.

4. A surgical instrument as claimed in claim 1 wherein the angle of convergence between said third planar surface and said axis is within the range of 20° to 35°, inclusive.

5. A surgical instrument as claimed in claim 4 wherein the angle of slope of said main cutting edge is less than 20°.

6. A surgical instrument as claimed in claim 5 wherein said first and second planar surfaces form at said main cutting edge a sharpness angle that is within the range of 40° to 50°, inclusive.

7. A surgical instrument as claimed in claim 6 wherein said angle of slope is approximately 18°, said sharpness angle is approximately 43° and said angle of convergence is approximately 30°.

8. A surgical instrument as claimed in claim 1 wherein said third surface forms corresponding acute angles with said first and second surfaces.

* * * * *